United States Patent [19]
Johnson

[11] Patent Number: 6,102,043
[45] Date of Patent: Aug. 15, 2000

[54] MALE CONDOM HARNESS

[76] Inventor: Joseph T. Johnson, 8028 Regent Park La., Charlotte, N.C. 28210

[21] Appl. No.: 09/373,417

[22] Filed: Aug. 12, 1999

Related U.S. Application Data

[63] Continuation-in-part of application No. 09/123,656, Jul. 28, 1998, Pat. No. 5,954,054.
[51] Int. Cl.$^7$ .................................................. A61F 6/04
[52] U.S. Cl. ......................................... 128/844; 128/918
[58] Field of Search .................................. 128/842, 844, 128/918; 604/347–353

[56] References Cited

U.S. PATENT DOCUMENTS

| | | |
|---|---|---|
| 4,919,149 | 4/1990 | Stang . |
| 5,314,447 | 5/1994 | Papurt . |
| 5,370,130 | 12/1994 | Hess . |
| 5,370,131 | 12/1994 | Hess ........................................ 128/844 |
| 5,458,114 | 10/1995 | Herr ........................................ 128/844 |
| 5,469,863 | 11/1995 | Shah . |
| 5,551,612 | 9/1996 | Hochfeld .................................. 128/844 |
| 5,651,374 | 7/1997 | Wester ..................................... 128/844 |
| 5,785,052 | 7/1998 | Johnson . |

*Primary Examiner*—Michael A. Brown
*Attorney, Agent, or Firm*—Christopher C. Dremann PC; Christopher C. Dremann

[57] ABSTRACT

A male condom harness securely retains a conventional male condom on the penis of the wearer, thereby effectively preventing unwanted pregnancy and protecting against communicable diseases transmitted by the exchange of bodily fluids. The male condom harness includes an annular retaining ring defining a longitudinal axis and having a first end and a second end. The male condom harness further includes at least one application handle attached to the retaining ring and depending outwardly therefrom. The application handle is utilized to properly apply the male condom harness on the penis of the wearer. In a preferred embodiment, the male condom harness further includes at least one retaining band attached to the retaining ring and depending generally rearwardly therefrom. In another preferred embodiment, the male condom harness further includes a pair of elongate retaining straps. Each of the retaining straps has a first end attached to the retaining ring and a second end that remains unattached. Preferably, the retaining ring has a gap formed therein between the pair of retaining straps. In another preferred embodiment, the male condom harness further includes at least one grommet positioned on the pair of retaining straps for cinching the retaining straps tightly against the base of the wearer's penis or behind the scrotum of the wearer. In yet another preferred embodiment, each of the retaining straps also has a helical groove forming a helical ridge thereon for increasing the friction force between the grommet and the retaining straps.

19 Claims, 5 Drawing Sheets

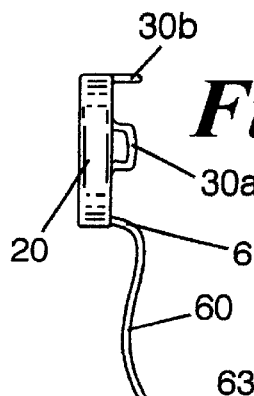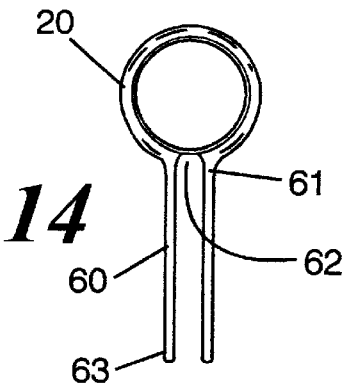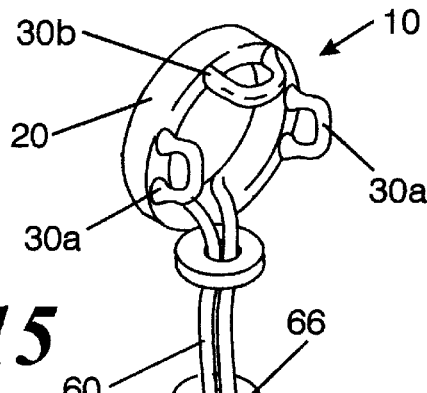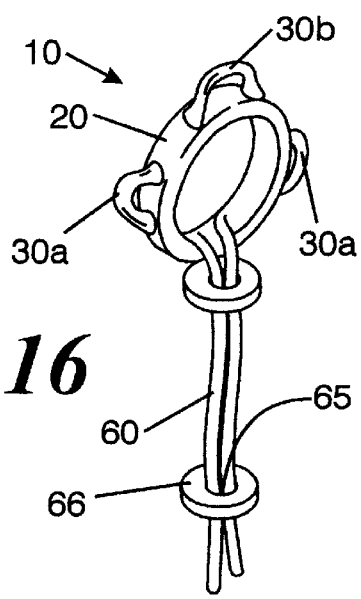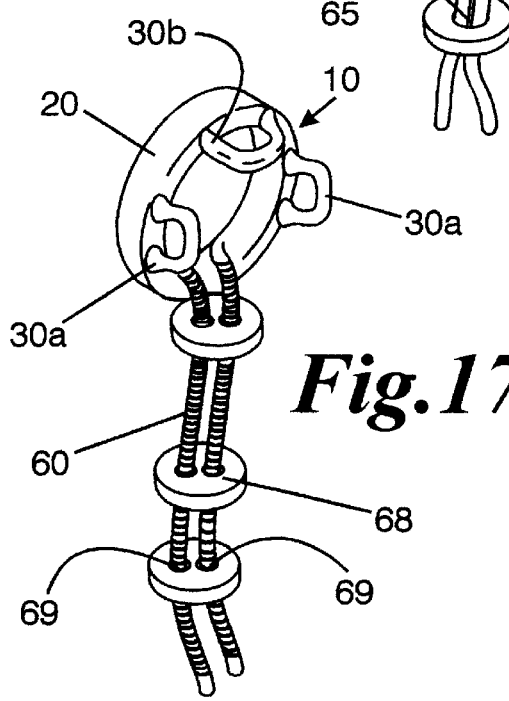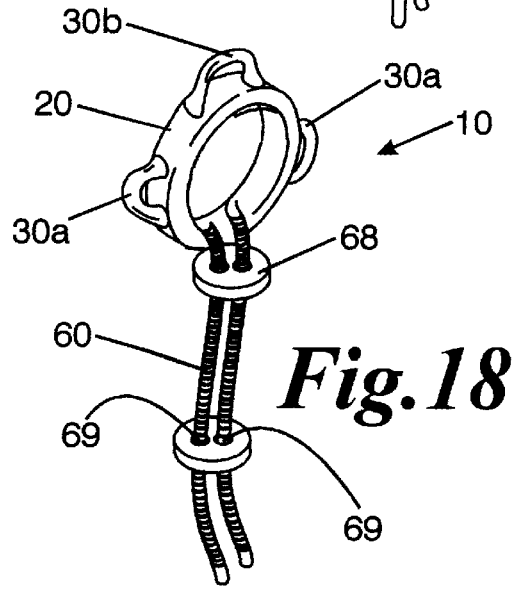

6,102,043

MALE CONDOM HARNESS

CROSS REFERENCE TO RELATED APPLICATION

This application is a continuation-in-part of U.S. patent application Ser. No. 09/123,656, filed Jul. 28, 1998, which issued Sep. 21, 1999, as U.S. Pat. No. 5,954,054.

FIELD OF THE INVENTION

The invention relates to a male condom harness that is designed and constructed to be used in conjunction with a male condom to effectively prevent unwanted pregnancy and to protect the wearer against communicable diseases, including viral diseases such as Human Immunodeficiency Virus (HIV), which has been known to lead to the development of Acquired Immunodeficiency Syndrome (AIDS). The wearer of the male condom harness is also effectively protected against other Sexually Transmitted Diseases (STDs) such as herpes, syphilis and gonorrhea.

BACKGROUND OF THE INVENTION

Sexual partners have long been mindful of unwanted pregnancy. Meanwhile, the public at large has become increasingly fearful of contracting communicable diseases, such as HIV, AIDS and other STDs, from sexual activity. It is well known that pregnancy occurs when the male sperm comes into contact with the female egg. It is also well known that STDs can be transmitted by the exchange of bodily fluids. Accordingly, the most widely used form of contraception and protection against STDs to date has been the male condom. Until now, however, there has not been a male condom that is highly effective in preventing unwanted pregnancy and at the same time guarding against the aforementioned public health concerns.

Known male condoms are primarily of two types. The first type consists of a thin, elongate, cylindrical body made of a form-fitting, fluid impervious material, such as latex, polyurethane or natural or synthetic rubber, which is open at one end and closed at the other end. The second type consists of a relatively thin, elongate, cylindrical body made of a loose-fitting, or "baggy", fluid impervious material, such as sheepskin or soft leather, which is open at one end and closed at the other end. The condom is open at one end for insertion of the penis and is closed at the other end to maintain a fluid-tight barrier between the wearer's penis and the sex organ, typically the mouth, vagina or anus, of the wearer's partner. Ideally, the condom prevents male sperm and other bodily fluids from being exchanged during sexual activity. For one reason or another, however, the male condoms available today do not adequately prevent the exchange of bodily fluids during sexual activity, and thus do not adequately prevent unwanted pregnancy or the transmission of STDs. In particular, the male condoms available today are not effective if they are improperly applied prior to sexual activity or are inadvertently removed during sexual activity.

The design and construction of the male condoms available today are not well adapted for their intended purpose. For example, the male condoms available today are generally difficult to properly apply to the penis of the wearer, particularly for those who are inexperienced or who may be under the influence of alcohol or drugs. If improperly applied, the condom may not provide an effective fluid-tight barrier, or worse yet, may become loose during the sexual activity, and rendered completely ineffective in preventing the exchange of bodily fluids. Even if properly applied to the penis of the wearer, known male condoms can be inadvertently removed during sexual activity if the condom is not securely retained on the wearer's penis. The likelihood that the condom will become loose or inadvertently removed is enhanced once the condom is subjected to the bodily fluids typically generated during sexual activity. Removal of the condom prior to completion of the sexual activity permits the bodily fluids of the wearer to come into contact with, and thus be exchanged with, the bodily fluids of the wearer's partner.

It is therefore apparent that there exists a need for a male condom harness that makes it easy to properly apply and securely retain a male condom on the penis of the wearer, thereby effectively preventing unwanted pregnancy and protecting against the transmission of STDs caused by the exchange of bodily fluids during sexual activity.

SUMMARY OF THE OBJECTS OF THE INVENTION

Accordingly, it is an object of the present invention to provide a male condom harness that makes it easy to properly apply a male condom on the penis of the wearer prior to sexual activity.

It is a further object of the present invention to provide a male condom harness that makes it easy to securely retain a male condom on the penis of the wearer during sexual activity and immediately thereafter.

It is yet another object of the present invention to provide a male condom harness that is designed and constructed to be used in conjunction with a male condom to effectively prevent unwanted pregnancy and to combat public health concerns, such as the transmission of STDs through the exchange of bodily fluids during sexual activity.

SUMMARY OF THE INVENTION

The invention is a male condom harness that makes it east to properly apply and to securely retain a male condom on the penis of a wearer, thereby effectively preventing unwanted pregnancy and protecting against communicable diseases transmitted by the exchange of bodily fluids. The male condom harness is made of an elastic, disposable, fluid impervious material forming an annular retaining ring defining a longitudinal axis and having a first end and a second end. In a preferred embodiment, the retaining ring is initially closed by a breakable-seal entrance shield adjacent each of the first end and the second end. The pair of opposed breakable-seal entrance shields store a liquid or gel lubricant or spermicide inside the body until the male condom harness is utilized and the entrance shields are broken, as will be described. In another preferred embodiment, the retaining ring of the male condom harness is open at both the first end and the second end.

The male condom harness further includes at least one application handle depending outwardly from the retaining ring. The application handle is utilized to properly apply the male condom on the penis of the wearer. In a preferred embodiment, the application handle extends radially and depends outwardly from the exterior surface of the retaining ring. In another preferred embodiment, the application handle extends longitudinally and depends generally rearwardly from the exterior surface of the retaining ring. The application handle may have any convenient configuration, but preferably is formed in a closed loop having a pair of opposed ends integrally formed with the retaining ring. Preferably, the at least one application handle includes a plurality of application handles that are circumferentially spaced about the retaining ring. For example, in one embodiment, the plurality of application handles includes a pair of diametrically opposed application handles. In an alternative embodiment, the plurality of application handles further includes a third application handle positioned medially between the pair of diametrically opposed application handles. In yet another embodiment, the plurality of application handles includes a first pair of diametrically opposed application handles and a second pair of diametrically opposed application handles positioned generally perpendicular to the first pair of diametrically opposed application handles.

In another preferred embodiment, the male condom harness further includes at least one thin, elongate retaining band extending outwardly from the retaining ring. The retaining band is utilized to securely retain the male condom on the penis of the wearer. The retaining band has a first end attached to the retaining ring and a second end opposite the first end attached to the retaining ring. Preferably, retaining band is made of an elastic, disposable, fluid impervious material. Most preferably, the retaining band is made of the same material as the retaining ring and is integrally formed with the retaining ring. The retaining band extends longitudinally and depends generally rearwardly from the exterior surface of the retaining ring. In a preferred embodiment, the first end of the retaining band and the second end of the retaining band are diametrically opposed. In another preferred embodiment, the first end of the retaining band and the second end of the retaining band form a closed loop that depends generally rearwardly from the exterior surface of the retaining ring. In yet another preferred embodiment, the male condom harness includes a pair of retaining bands formed in a closed loop that depend generally rearwardly from the exterior surface of the retaining ring at diametrically opposed positions.

In another preferred embodiment, the male condom harness further includes a pair of thin, elongate retaining straps extending outwardly from the retaining ring. The first end of each retaining strap is attached to the retaining ring and the second end of each retaining strap remains unattached, for a purpose to be described hereinafter. The retaining straps are utilized to securely retain the male condom on the penis of the wearer. The retaining straps may be tied together in a tight knot below or above the base of the wearer's penis. Alternatively, the retaining straps may be wrapped around the wearer's scrotum from above or below the base of the penis and then tied together in a tight knot behind the wearer's scrotum. Alternatively, the retaining straps may be wrapped around the wearer's scrotum from below the base of the penis and back around the scrotum, and then tied together in a tight knot above the base of the wearer's penis. In a preferred embodiment, the retaining straps include at least one grommet having at least one hole therethrough for positioning the grommet on both retaining straps. The at least one grommet is utilized to cinch the retaining straps against the wearer's penis or scrotum prior to tying the retaining straps in a tight knot. In an alternative embodiment, the retaining straps have a helical groove forming a helical ridge thereon for engaging the at least one grommet. In other preferred embodiments, the retaining straps include two or three grommets for cinching the retaining straps below the wearer's penis, behind the wearer's scrotum or above the wearer's penis, as applicable.

BRIEF DESCRIPTION OF THE DRAWINGS

In view of the above and other objects which will more readily appear as the nature of the invention is better understood, the invention consists in the novel combination and arrangement of parts hereinafter more fully described, illustrated and claimed with reference being made to the attached drawings in which:

FIG. 13 is a side elevation view of the male condom harness of FIG. 11;

FIG. 14 is a rear elevation view of the male condom harness of FIG. 11;

FIG. 15 is a perspective view of an alternative embodiment of the male condom harness of FIG. 11;

FIG. 16 is a perspective view of an alternative embodiment of the male condom harness of FIG. 12;

FIG. 17 is a perspective view of another alternative embodiment of the male condom harness of FIG. 11; and FIG. 18 is a perspective view of another alternative embodiment of the male condom harness of FIG. 12.

DETAILED DESCRIPTION OF THE PREFERRED EMBODIMENTS

Figure 1:
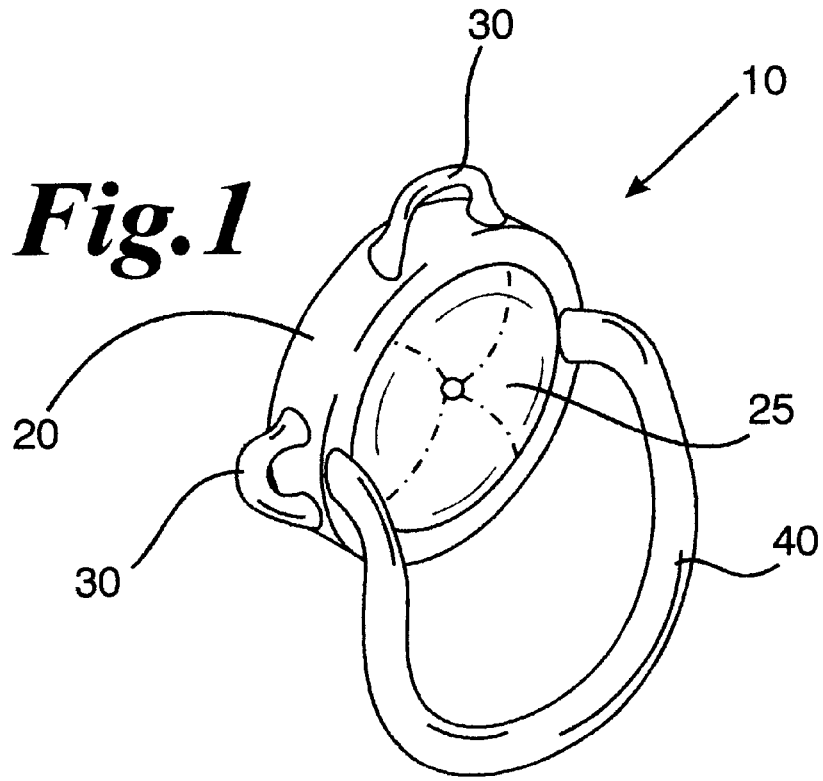
FIG. 1 is a perspective view of a preferred embodiment of a male condom harness according to the invention including a pair of opposed breakable-seal entrance shields.
Figure 2:
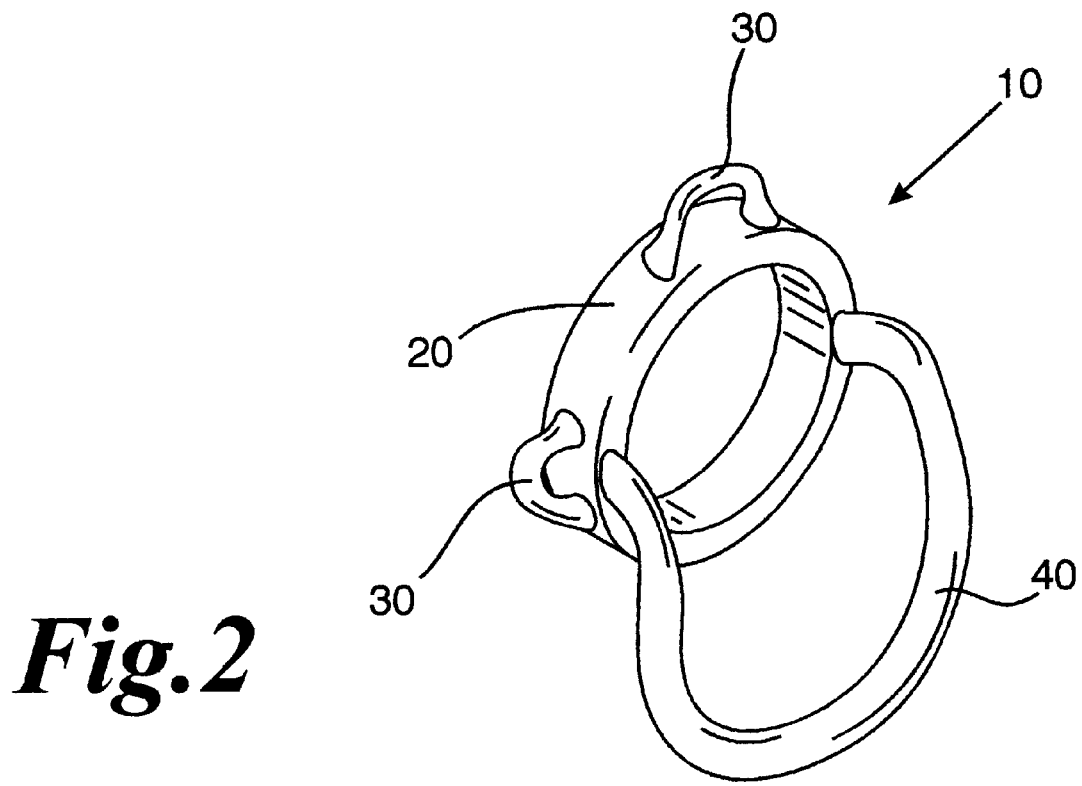
FIG. 2 is a perspective view of another preferred embodiment of a male condom harness according to the invention.

Preferred embodiments of the present invention will be described more fully hereafter followed by a brief description of a number of alternative preferred embodiments. However, the invention should not be construed as being limited by the preferred embodiments described herein. Rather, it is intended that the invention be construed broadly to encompass any and all embodiments of a male condom harness having the features described and illustrated herein which is within the skill of a person of ordinary skill in the relevant art. In the description, like reference numerals designate like or corresponding parts throughout the several figures. It is also to be understood that positional terms such as "top", "bottom", "side", "front" and "rear" are used in the description for purposes of locating one element relative to another, and thus, are not to be construed as limiting terms. Finally, it should be understood that the illustrations provided in the figures are for the purpose of describing preferred embodiments of the invention, and thus, are not intended to limit the invention in any manner.

Figure 3:
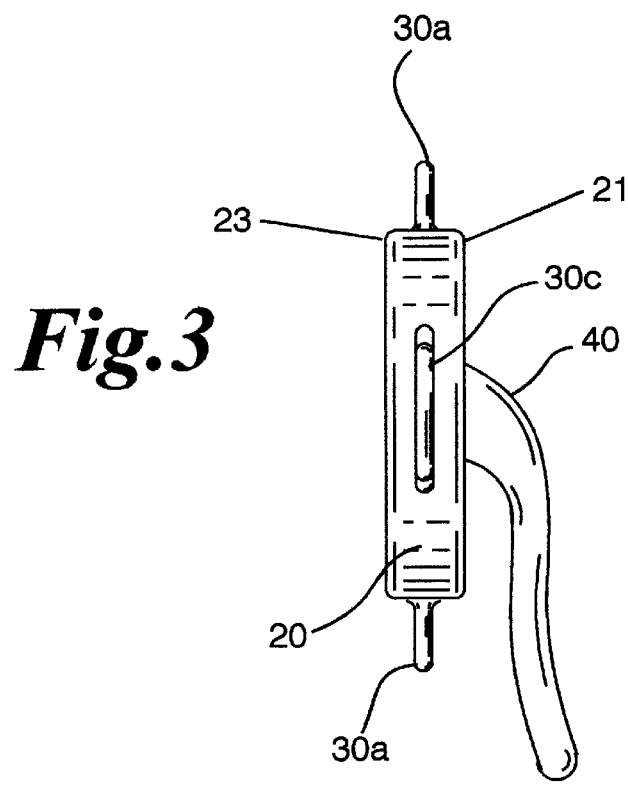
FIG. 3 is a side elevation view of the male condom harness of FIG. 1.
Figure 4:
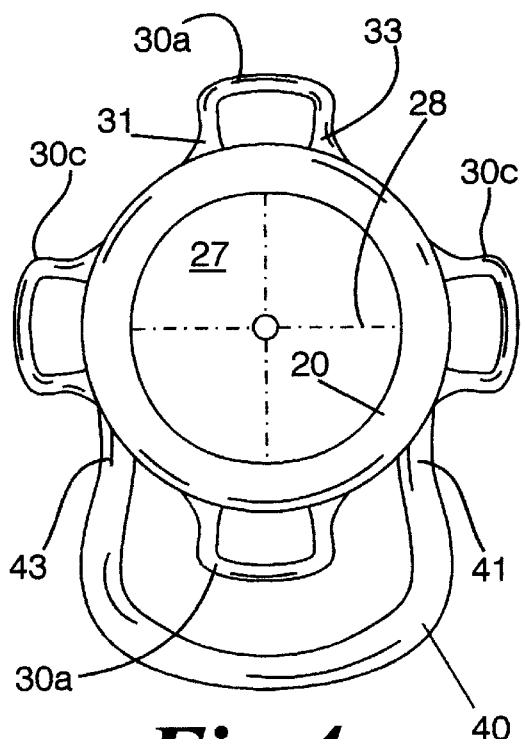
FIG. 4 is a rear elevation view of the male condom harness of FIG. 1.
Figure 5:
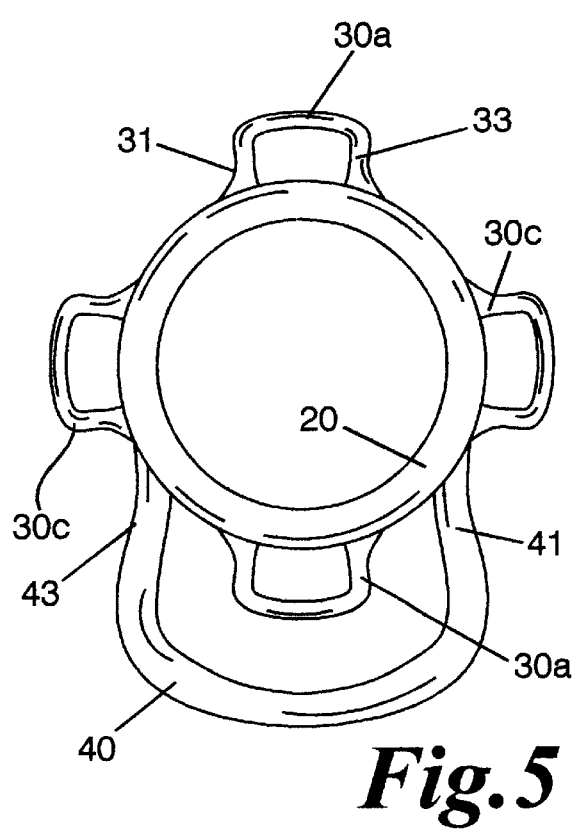
FIG. 5 is a rear elevation view of the male condom harness of FIG. 2.

Referring now to the accompanying figures, the invention is a male condom harness, indicated generally at 10, for use in conjunction with a male condom for preventing unwanted pregnancy and for protecting against the transmission of STDs, such as AIDS, through the exchange of bodily fluids, such as saliva, perspiration, sperm and blood, during sexual activity. Preferably, the male condom harness 10 is made of an elastic, disposable, fluid impervious material. Most preferably, the male condom harness 10 is made of a dipped or molded, uninterrupted liquid latex, liquid polyurethane or natural or synthetic rubber material that is impervious to fluids, and in particular is impervious to male sperm and to other bodily fluids that transmit liquid-born viruses, such as STDs. In the broadest sense, the male condom harness 10 comprises an annular retaining ring 20 and at least one application handle 30 depending outwardly from the retaining ring. The male condom harness 10 may be used to apply pressure to the base of the penis of the wearer, thereby increasing stimulation of the penis and maintaining the penis erect. Alternatively, the male condom harness may be used in conjunction with a conventional male condom, such as a form-fitting or loose-fitting (e.g., "baggy") condom, to securely retain the condom on the penis of the wearer. For purposes of the description of the preferred embodiments illustrated herein, the male condom harness 10 is positioned over a conventional male condom to securely retain the condom on the penis of the wearer. Thus, it is less likely that the male condom will be inadvertently removed during sexual activity. In a preferred embodiment, the male condom harness 10 further comprises a pair of opposed breakable-seal entrance shields 25 (FIGS. 1, 3, and 4 ). In another preferred embodiment, the male condom harness 10 further comprises at least one retaining band 40 depending outwardly from the retaining ring 20 (FIGS. 1–10). In another preferred embodiment, the male condom harness 10 further comprises a pair of retaining straps 60 depending outwardly from the retaining ring 20 (FIGS. 11–18 ). In another preferred embodiment, the male condom harness 10 further comprises at least one grommet 66, 68 positioned on the pair of retaining straps 60 (FIGS. 15–18 ). In yet another preferred embodiment, each of the pair of retaining straps 60 of the male condom harness 10 comprises a helical groove forming a helical ridge 67 on the retaining straps 60 (FIGS. 17 and 18 ).

In the preferred embodiment shown in FIGS. 1, 3 and 4, the male condom harness 10 comprises an annular retaining ring 20 defining a longitudinal axis and having a first end 21 (FIG. 3) and a second end 23 (FIG. 3). The male condom harness 10 further comprises at least one application handle 30 depending outwardly from the retaining ring 20, as will be described hereinafter. The retaining ring 20 is initially closed by a pair of opposed, breakable-seal entrance shields 25. Each of the entrance shields 25 comprises a plurality of flaps 27 (FIG. 4) joined together along perforated edges 28 (FIG. 4) to form a generally circular, perforated entrance shield. An example of such a breakable-seal entrance shield 25 is disclosed and shown in U.S. patent application Ser. No. 09/123,656, now U.S. Pat. No. 5,954,054, the disclosure of which is expressly incorporated herein. The entrance shields 25 are attached to the interior surface of the retaining ring 20 adjacent each of the first end 21 and the second end 23 of the retaining ring. The pair of opposed breakable-seal entrance shields 25 store a liquid or gel lubricant or spermicide inside the retaining ring 20 until the male condom harness 10 is utilized and the entrance shields are broken. The entrance shields 25 are broken when the male condom harness 10 is positioned on the penis of the wearer over the male condom. In particular, the entrance shield 25 adjacent the first end 21 of the retaining ring 20 is broken as the tip of the wearer's penis penetrates the male condom harness 10, thereby releasing the lubricant or spermicide inside the retaining ring to flow onto the exterior surface of the male condom. The entrance shield 25 adjacent the second end 23 of the retaining ring 20 is then broken as the tip of the wearer's penis penetrates the male condom harness 10. In the preferred embodiment shown in FIGS. 2 and 5, the male condom harness 10 does not comprise a pair of opposed, breakable-seal entrance shields 25. Thus, the male condom harness 10 shown in FIGS. 2 and 5 does not include a lubricant or spermicide to be applied to the exterior surface of the penis of the wearer or to the exterior surface of a male condom positioned on the penis of the wearer.

The male condom harness 10 further comprises at least one application handle 30 depending outwardly from the retaining ring 20. An example of such an application handle 30 is described and shown in greater detail in U.S. patent application Ser. No. 09/123,656, now U.S. Pat. No. 5,954,054. The application handle 30 is utilized to properly apply the male condom on the penis of the wearer. Preferably, the application handle 30 is made of an elastic, disposable, fluid impervious material. Most preferably, the application handle 30 is made of the same material as the retaining ring 20 and is integrally formed with the retaining ring. In the preferred embodiments of the male condom harness 10 shown in FIGS. 1–9, 12, 16 and 18, the application handle 30 extends radially and depends outwardly from the exterior surface of the retaining ring 20. In the preferred embodiments shown in FIGS. 10–11 , 13–15 and 17, the application handle 30 extends longitudinally and depends generally rearwardly from the exterior surface of the retaining ring 20. The application handle 30 may have any convenient configuration, but preferably is formed in a closed loop having a pair of opposed ends 31, 33 integrally formed with the retaining ring 20. Preferably, the at least one application handle 30 comprises a plurality of application handles that are circumferentially spaced about the retaining ring 20. For example, in the preferred embodiments of the male condom harness 10 shown in FIGS. 1–10, the plurality of application handles 30 comprises a first pair of diametrically opposed application handles 30*a* and a second pair of diametrically opposed application handles 30*c* positioned generally perpendicular to the first pair of diametrically opposed application handles. In the preferred embodiments of the male condom harness shown in FIGS. 11–18, the plurality of application handles 30 comprises the first pair of diametrically opposed application handles 30*a* and a third application handle 30*b* positioned medially between the first pair of application handles 30*a*.

In the preferred embodiments shown in FIGS. 1–10, the male condom harness 10 further comprises at least one thin, elongate retaining band 40 extending outwardly from the retaining ring 20. An example of such a retaining band 40 is described and shown in greater detail in U.S. patent application Ser. No. 09/123,656, now U.S. Pat. No. 5,954,054.

The retaining band 40 is utilized to securely retain the male condom on the penis of the wearer. The retaining band 40 has a first end 41 attached to the retaining ring 20 and a second end 43 opposite the first end that is likewise attached to the retaining ring. Preferably, the retaining band 40 is made of an elastic, disposable, fluid impervious material. Most preferably, the retaining band 40 is made of the same material as the retaining ring 20 and is integrally formed with the retaining ring. The retaining band 40 extends longitudinally and depends generally rearwardly from the exterior surface of the retaining ring 20. In the preferred embodiments of the male condom harness 10 shown in FIGS. 1–5, the first end 41 of the retaining band 40 is diametrically opposed to the second end 43 of the retaining band. In the preferred embodiments of the male condom harness 10 shown in FIGS. 6–10, the first end 41 of the retaining band 40 and the second end 43 of the retaining band form a closed loop that depends generally rearwardly from the exterior surface of the retaining ring 20 adjacent one of the application handles 30. In the preferred embodiments of the male condom harness 10 shown in FIGS. 6 and 9, the at least one retaining band 40 comprises a first retaining band 40a and a second retaining band 40b each formed in a closed loop that depends generally rearwardly from the exterior surface of the retaining ring 20 at diametrically opposed positions.

Figure 6:
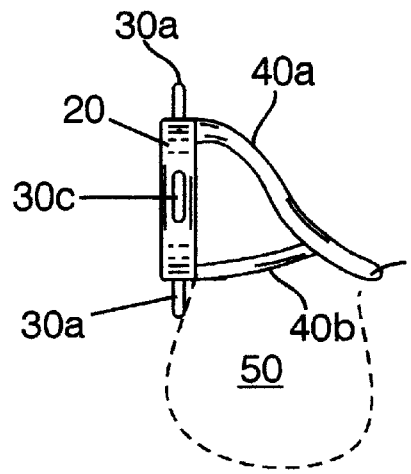
FIG. 6 is a side elevation view of an alternative embodiment of the male condom harness of FIG. 1 illustrating a preferred method of securely retaining a male condom on the penis of the wearer.
Figure 8:
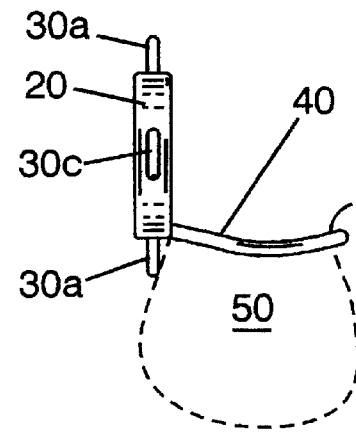
FIG. 8 is a side elevation view of the male condom harness of FIG. 7 illustrating another alternative method of securely retaining a male condom on the penis of the wearer.
Figure 7:
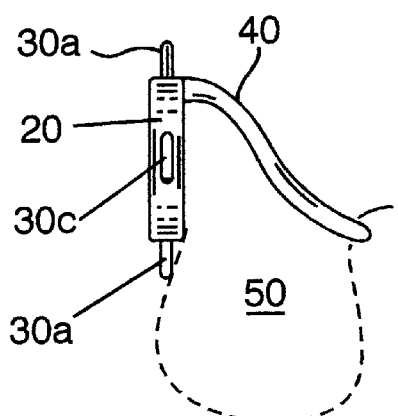
FIG. 7 is a side elevation view of another alternative embodiment of the male condom harness of FIG. 1 illustrating an alternative method of securely retaining a male condom on the penis of the wearer.
Figure 9:
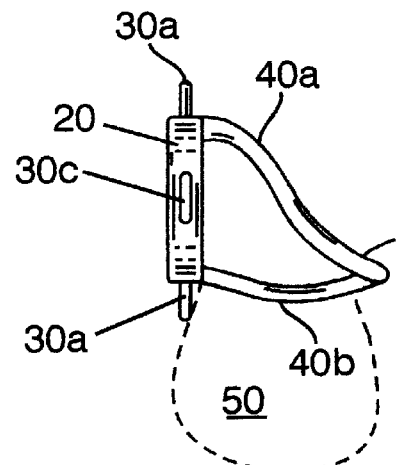
FIG. 9 is a side elevation view of another alternative embodiment of the male condom harness of FIG. 1 illustrating yet another alternative method of securely retaining a male condom on the penis of the wearer.
Figure 10:
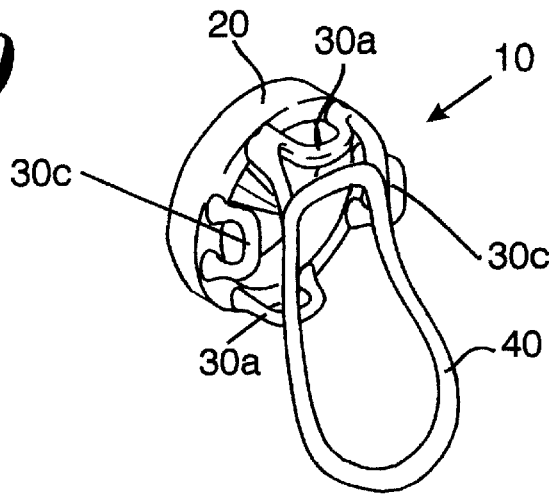
FIG. 10 is a perspective view of another preferred embodiment of a male condom harness according to the invention.
Figure 11:
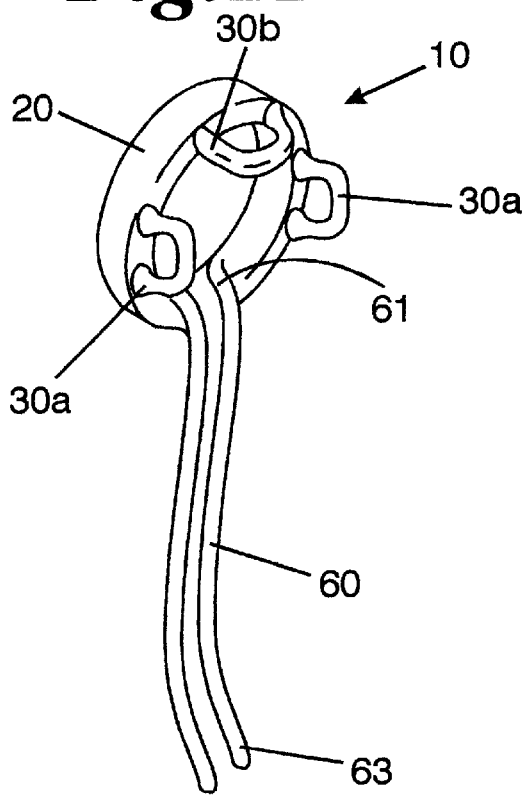
FIG. 11 is a perspective view of another preferred embodiment of a male condom harness according to the invention.
Figure 12:
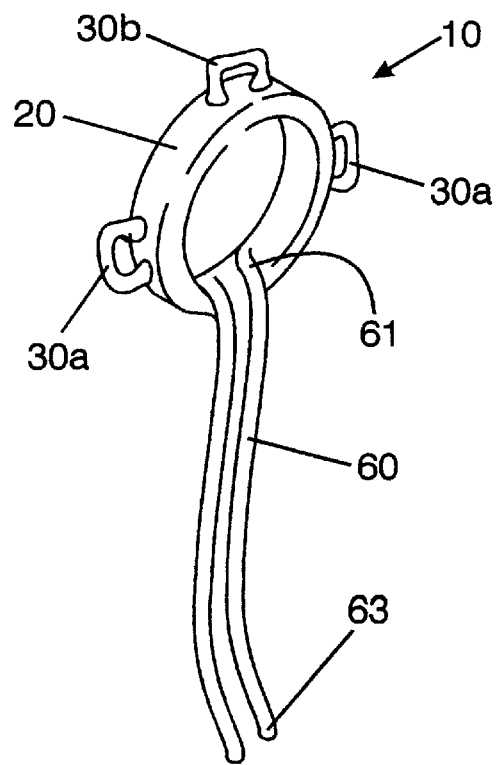
FIG. 12 is a perspective view of another preferred embodiment of a male condom harness according to the invention.

A preferred method of utilizing a preferred embodiment of the male condom harness to securely retain a male condom on the penis of the wearer is illustrated in FIG. 6. Once the male condom is positioned on the penis of the wearer and the male condom harness 10 is positioned over the male condom, the first retaining band 40a is looped around the scrotum 50 of the wearer from above the base of the wearer's penis. The second retaining band 40b, which is attached to the first retaining band 40a at two locations medially between the first end 41 and the second end 43 of the first retaining band 40a, is then looped around the scrotum of the wearer from below the base of the wearer's penis. Accordingly, the male condom is securely retained on the penis of the wearer both during and after sexual activity. An alternative method of utilizing another preferred embodiment of the male condom harness 10 to securely retain a male condom on the penis of the wearer is illustrated in FIG. 7. Once the male condom harness 10 is positioned over the male condom, the single retaining band 40 is looped around the scrotum 50 of the wearer from above the base of the wearer's penis. Another alternative method of utilizing the preferred embodiment of the male condom harness shown in FIG. 7 to securely retain a male condom on the penis of the wearer is illustrated in FIG. 8. Once the male condom harness 10 is positioned over the male condom, the single retaining band 40 is looped around the scrotum 50 of the wearer from below the base of the wearer's penis. Yet another alternative method of utilizing yet another preferred embodiment of the male condom harness 10 to securely retain a male condom on the penis of the wearer is illustrated in FIG. 9. Once the male condom harness 10 is positioned over the male condom, the first retaining band 40a is looped around the scrotum 50 of the wearer from above the base of the wearer's penis. The second retaining band 40b, which is attached to the first retaining band 40a at a single location opposite the first end 41 and the second end 43 of the first retaining band 40a, is then looped around the scrotum of the wearer from below the base of the wearer's penis.

In the preferred embodiments shown in FIGS. 11–18, the male condom harness 10 further comprises a pair of thin, elongate retaining straps 60 extending outwardly from the retaining ring 20. The first end 61 of each retaining strap 60 is attached to the retaining ring 20 and the second end 63 of each retaining strap remains unattached, for a purpose to be described hereinafter. Preferably, the retaining straps 60 are made of an elastic, disposable, fluid impervious material. Most preferably, the retaining straps 60 are made of the same material as the retaining ring 20 and are integrally formed with the retaining ring. As best shown in FIGS. 13 and 14, the pair of retaining straps 60 preferably depend outwardly from the retaining ring 20 at a location opposite the medial application handle 30b. A recess, or gap 62 (FIG. 14), is formed in the retaining ring 20 such that the pair of retaining straps 60 close the gap 62, and thereby constrict the retaining ring on the wearer's penis, when the retaining straps are tied together in a tight knot. Thus, an increased pressure is applied to the base of the wearer's penis by the male condom harness 10 and the male condom is further secured on the penis of the wearer. Thus, it is less likely that the adjustable male condom will be inadvertently removed during sexual activity. The retaining straps 60 are utilized to securely retain the male condom on the penis of the wearer. Obviously, the pair of retaining straps 60 can be tied together in a number of different ways to further secure the male condom harness 10 and the male condom on the penis of the wearer. Examples of various preferred methods of tying the retaining straps 60 of the male condom harness 10 shown in FIGS. 11–18 together in a tight knot to securely retain a male condom on the penis of the wearer are illustrated in FIGS. 5–9 of co-pending U.S. patent application Ser. No. 09/372, 953, the disclosure of which is expressly incorporated herein. For example, the retaining straps 60 may be tied together in a tight knot below the base of the penis of the wearer adjacent the scrotum 50 of the wearer. Alternatively, the retaining straps 60 may be tied together in a tight knot above the base of the wearer's penis opposite the scrotum 50 of the wearer. Alternatively, the retaining straps 60 may be wrapped around the wearer's scrotum 50 from above or below the base of the penis in opposite directions and then tied together in a tight knot behind the wearer's scrotum. Alternatively, the retaining straps 60 may be wrapped around the wearer's scrotum 50 from below the base of the penis in opposite directions, crossed over, wrapped around the scrotum again in opposite directions and then tied together in a tight knot above the base of the penis opposite the scrotum 50 of the wearer.

In the preferred embodiments of the male condom harness 10 shown in FIGS. 15 and 16, the retaining straps 60 comprise at least one grommet 66 for further securing the male condom harness and the male condom on the penis of the wearer. The grommet 66 has a hole 65 formed therethrough for positioning the grommet on both retaining straps 60. The at least one grommet 66 is positioned on the pair of retaining straps 60 by inserting the retaining straps into the single hole 65 formed through the grommet. The at least one grommet 66 is then moved along the pair of retaining straps 60 in the direction of the retaining ring 20 to cinch the retaining straps against the base of the penis or behind the scrotum 50, as applicable. Thus, the male condom harness 10, and consequently the male condom, may be securely retained on the penis of the wearer in the manner illustrated in FIGS. 5–9 of co-pending U.S. patent application Ser. No. 09/372,953. In the preferred embodiments of the male condom harness 10 shown in FIGS. 17 and 18, the retaining straps 60 comprise at least one grommet 68 for further securing the male condom harness and the male condom on the penis of the wearer. The grommet 68 has a pair of holes 69 formed therethrough for positioning the grommet on both retaining straps 60. In addition, each of the pair of retaining straps 60 has a continuous, helical groove forming a helical ridge 67 thereon. The ridge 67 creates an increased friction force between the at least one grommet 68 and the retaining straps 60. The at least one grommet 68 is positioned on the pair of retaining straps 60 by inserting the retaining straps into the pair of holes 69 formed through the grommet. The at least one grommet 68 is then moved along the pair of retaining straps 60 in the direction of the retaining ring 20 to cinch the retaining straps against the base of the penis or behind the scrotum 50, as applicable. Thus, the male condom harness 10, and consequently the male condom, may be securely retained on the penis of the wearer in the manner illustrated in FIGS. 5–9 of co-pending U.S. patent application Ser. No. 09/372,953.

From the forgoing, it is readily apparent that the present invention provides a male condom harness that is easy to properly apply prior to sexual activity. It is further apparent that the present invention provides a male condom harness that can be used in conjunction with a conventional male condom to securely retain the male condom on the penis of the wearer before, during and after sexual activity, thereby effectively preventing unwanted pregnancy as well as combating public health concerns. It is to be understood that the forgoing description and specific embodiments shown herein are merely illustrative of the best mode of the invention and the principals thereof, and that various modifications and additions may be made by those skilled in the art without departing unnecessarily from the spirit and scope of the invention, which is intended to be limited only by the scope of the appended claims.

That which is claimed is:

1. A male condom harness comprising
   an annular retaining ring defining a longitudinal axis;
   a pair of opposed, breakable-seal entrance shields attached to and closing said retaining ring;
   at least one application handle attached to said retaining ring; and
   at least one retaining band attached to said retaining ring and depending generally rearwardly therefrom, said retaining band formed in a closed loop and attached to said retaining ring adjacent said at least one application handle.

2. A male condom harness according to claim 1 wherein each of said pair of entrance shields comprises a plurality of flaps joined together along perforated edges.

3. A male condom harness according to claim 1 wherein said at least one application handle extends radially and depends generally outwardly from the exterior surface of said retaining ring.

4. A male condom harness according to claim 1 wherein said at least one application handle extends longitudinally and depends generally rearwardly from the exterior surface of said retaining ring.

5. A male condom harness according to claim 1 wherein said at least one application handle comprises a plurality of application handles circumferentially spaced about said retaining ring.

6. A male condom harness according to claim 5 wherein said plurality of application handles consists of a pair of diametrically opposed application handles.

7. A male condom harness according to claim 5 wherein said plurality of application handles consists of a first pair of diametrically opposed application handles and a second pair of diametrically opposed application handles positioned generally perpendicular to said first pair of application handles.

8. A male condom harness comprising
   an annular retaining ring defining a longitudinal axis;
   at least one application handle attached to said retaining ring; and
   a pair of retaining straps, each of said pair of retaining straps having a first end attached to said retaining ring and a second end that remains unattached.

9. A male condom harness according to claim 8 further comprising a pair of opposed, breakable-seal entrance shields attached to and closing said retaining ring.

10. A male condom harness according to claim 9 wherein each of said pair of entrance shields comprises a plurality of flaps joined together along perforated edges.

11. A male condom harness according to claim 8 wherein said at least one application handle extends radially and depends generally outwardly from the exterior surface of said retaining ring.

12. A male condom harness according to claim 8 wherein said at least one application handle extends longitudinally and depends generally rearwardly from the exterior surface of said retaining ring.

13. A male condom harness according to claim 8 wherein said at least one application handle comprises a plurality of application handles circumferentially spaced about said retaining ring.

14. A male condom harness according to claim 13 wherein said plurality of application handles consists of a pair of diametrically opposed application handles and an application handle positioned medially between said pair of application handles.

15. An adjustable male condom according to claim 8 wherein said retaining ring has a gap formed therein medially between said pair of retaining straps.

16. A male condom harness according to claim 8 further comprising at least one grommet positioned on said pair of retaining straps.

17. A male condom harness according to claim 16 wherein said at least one grommet has a single hole formed therethrough for receiving said pair of retaining straps therein.

18. A male condom harness according to claim 16 wherein said at least one grommet has a pair of holes formed therethrough for receiving said pair of retaining straps therein.

19. A male condom harness according to claim 8 wherein each of said pair of retaining straps has a helical groove forming a helical ridge thereon.

* * * * *